United States Patent [19]

Nicolaou et al.

[11] 4,256,883
[45] Mar. 17, 1981

[54] PYRIDOZA PROSTACYCLIN ANALOGUES AND N-OXIDES THEREOF

[75] Inventors: Kyriacos C. Nicolaou, Havertown; William E. Barnette, Levittown, both of Pa.; Ronald L. Magolda, Vineland, N.J.

[73] Assignee: Research Corporation, New York, N.Y.

[21] Appl. No.: 20,543

[22] Filed: Mar. 14, 1979

[51] Int. Cl.$^3$ .................. C07D 237/26; A61K 31/50
[52] U.S. Cl. .............................. 544/235; 260/346.22; 424/250; 560/121; 544/225; 544/226
[58] Field of Search ......................................... 544/235

[56] References Cited
PUBLICATIONS

Faragher et al., Chem. Abs. 86, 5392q (1976).

*Primary Examiner*—Mark L. Berch
*Attorney, Agent, or Firm*—Oblon, Fisher, Spivak, McClelland & Maier

[57] ABSTRACT

Stable biologically active aromatic prostacyclin analogues of the formula

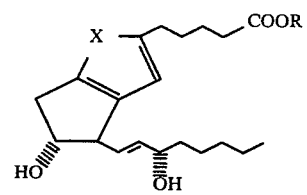

wherein X represents

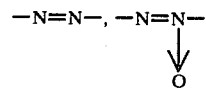

and R represents hydrogen, a pharmaceutically acceptable cation or a pharmaceutically acceptable lower alkyl group, are useful in the treatment of blood platelet aggregation and vascular constriction.

8 Claims, No Drawings

PYRIDOZA PROSTACYCLIN ANALOGUES AND N-OXIDES THEREOF

This invention was made in the course of sponsorship by the Department of Health, Education and Welfare of the United States, and support therefor is hereby acknowledged.

BACKGROUND OF THE INVENTION

1. Field of the Invention

This invention relates to stable aromatic prostacyclin analogues which are active as inhibitors of blood platelet aggregation and which show arterial dilation activities.

2. Description of the Prior Art

The prostaglandins were first discovered in the 1920's and have proven since then to be among the most ubiquitous pharmaceutically active compounds ever tested. Their use and the use of analogues and derivatives thereof, has been suggested in as wide a range of applications as fertility control, induction of labor, regulation of blood pressure, regulation of blood clotting, control of asthma, anticonvulsion, antidepressing action and many others. A new compound has recently been discovered (Nature 263, 663 (1976); *Prostaglandins*, vol. 12, 685 and 715 (1976); Chem. and Engineering News, Dec. 20, 1976) which belongs to the general family of prostaglandins. The compound has been named prostacyclin and its structure has been proven by synthesis (Johnson, et. al, *Prostaglandins*, 12, 915 (1976); Corey, et al, J. Amer. Chem. Soc., 99, 2006 (1977)) to be that of formula I. (The numbering system for prostacyclins is given for reference):

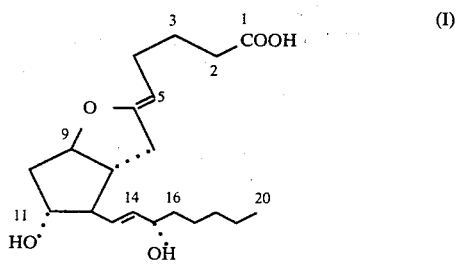

Its generic name is 6,9α-oxido-11α,15α-dihydroxy-prosta (Z)5, E(13)-dienoic acid. Prostacyclin is the most potent inhibitor of blood platelet aggregation of all the prostaglandins discovered to date. It has also been shown that prostacyclin destroys platelet aggregates after they have formed and that it has, in addition, a powerful action as a dilator of blood vessels. Prostacyclin thus appears to act in exactly opposite ways to thromboxane $A_2$, another recently discovered member of the prostaglandin family. Thromboxane $A_2$ causes platelet aggregation and simultaneously acts as powerful constrictor of arteries. Both prostacyclin and thromboxane $A_2$ are derived biosynthetically from a common intermediate called endoperoxide, and they are decomposed by water to prostaglandins (Scheme I). The balance between the levels of prostacyclin and thromboxane $A_2$, appears to maintain a finely tuned equilibrium between blood platelet aggregation versus dissolution and arterial constriction versus dilation.

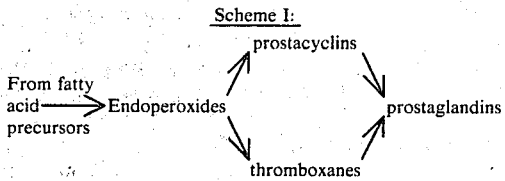

Thromboxane $A_2$ generated by platelets promotes aggregation while prostacyclin produced by vascular endothelium inhibits aggregation. It has also been proposed (S. Moncada et al, Lancet I, 18 (1977)) that (1) the basal formation of prostacyclin by vascular endothelium may be important in the maintenance of the normal integrity of vessel walls by inhibiting the adherence of platelets, (2) prostacyclin may normally limit thrombus formation, and (3) when a vessel wall is damaged, the formation of a normal hemostatic plug may be assisted by diminished prostacyclin production.

In addition to its effects on platelets, prostacyclin may play a crucial role in preventing gastric ulceration by inhibiting secretion, in blood pressure regulation by control of vascular tone, and in inflammation by inhibiting protease secretion of polymorphonuclear leucocytes. These and several other important physiological processes may be regulated by the opponent actions of thromboxane $A_2$ (TXA$_2$) and prostacyclin (PCI$_2$). The use of prostacyclins has therefore been suggested in the treatment of blood clotting in diseased vessels of patients with cardiovascular problems. Since prostacyclin has retroactive action and not only inhibits blood clotting but also dissolves already formed clots, it can be used in heart attack cases and artherosclerosis. Increased susceptibility of platelets to aggregation accompanies vascular complications in diabetes, in cerebral strokes associated with essential hypertension and in post heart attack cases. These are other areas where prostacyclin or its analogues can be highly beneficial. The main drawback of the use of prostacyclin for these applications is its very short biological half-life of 2 minutes. This prevents the externally provided drug from reaching its target tissues intact. The need to maintain the drug in a totally anhydrous condition also prevents its ready shipment, storage and testing for pharmacological applications. If an analogue or derivative of prostacyclin can be found which is stable and shows similar effects on blood platelets and arteries, it would have wide applications in pharmacology and the treatment of cardiovascular and related diseases.

Another application for a stable analogue of prostacyclin would be its use as an inhibitor of blood platelet aggregation in externally circulated blood by kidney dialysis machines or heart-lung machines.

Prostacyclin analogues may also be useful in the treatment of several types of shock. For example, in hemorrhagic shock, vasoconstriction may severely limit the flow of blood to the gut and kidneys. Replacement of the blood volume lost will easily redilate the gut vessels but flow through the kidney may be impeded for a long period of time. During this interval the kidneys may infarct. In addition, prolonged vasoconstriction in the gut region may release proteases from liver and pancreatic lysozomes. Prostacyclin or its analogues may attenuate these deleterious effects by maintaining a small amount of blood flow through these areas.

A number of stable analogues of prostacyclin of varying biological activity has been prepared. See for example Nicolaou et al., Angew. Chem., Int. Ed. Engl. 17, 293 (1978) for a general review. Among these are thia-prostacyclins (II), discussed by Nicolaou and coworkers in J. Amer. Chem. Soc. 99, 7736 (1977). The thia-prostacyclins are also the subject of copending application Serial No. 886,141, filed Mar. 13, 1978 and which is herein incorporated by reference.

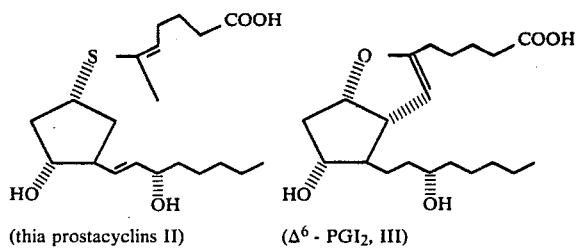

(thia prostacyclins II)    ($\Delta^6$ - PGI$_2$, III)

Another analogue of natural prostacyclin is $\Delta^6$ prostacyclin ($\Delta^6$—PGI$_2$, (III)) prepared by Shimoji and coworkers (J. Amer. Chem. Soc., 100, 2547 (1978). Compound III, $\Delta^6$—PGI$_2$, appears to have recently been isolated from rat stomach homogenates and its presumed structure was identified by Sih et al. (J. Amer. Chem. Soc., 100, 643 (1978)).

Upjohn scientists have recently reported the nitrogen-containing prostacyclin analogues IV and V; (Bundy, G., Tetrahedron Letters, 1371 (1978)):

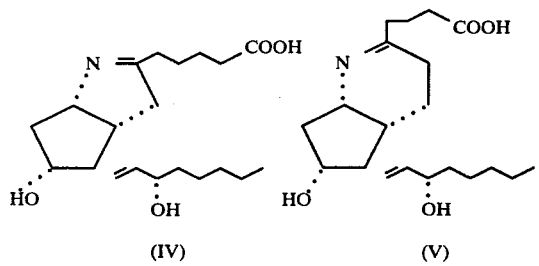

(IV)    (V)

Analogues IV and V showed high stability and potency in inhibiting platelet aggregation.

All of the aforementioned analogues (II–V) showed biological activity mimicking prostacyclin action. Other, somewhat less, active analogues of prostacyclin have also been prepared: dihydroprostacyclin (VI) (Corey et al, J. Amer. Chem. Soc, 99, 2006 (1977)) and (4E)—isoprostacyclin (VII), disclosed in U.S. application Ser. No. 886,143, filed Mar. 13, 1978.

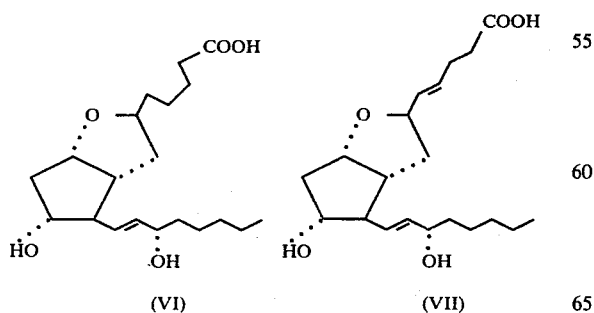

(VI)    (VII)

The present inventors have compared the biological activity for all stable prostacyclin analogues reported to date (II–VII, plus others listed in the aforementioned Nicolaou et al article in Angewandte Chemie). They have sought to elucidate the structures which yield the highest biological activity and have discovered that the most potent ones are those retaining $Sp^2$—hybridized C-6. Natural prostacyclin, of course, contains an $Sp^2$ hybridized C-6; compounds II–V do so as well. Compounds VI and VII on the other hand do not have a C-6 $Sp^2$-carbon and show less biological activity. Based on this discovery, the present inventors have discovered that both high stability and biological activity can be obtained generally when the labile cyclic ether rings of natural prostacyclin is replaced by a fully aromatic ring, a fact which among others assures the presence of an $Sp^2$ hybridized C-6. The presence of an aromatic ring instead of a labile cyclic enol ether ring also ensures stability in aqueous, physiological media and renders the analogues useful for a large number of applications.

SUMMARY OF THE INVENTION

Accordingly it is an object of the invention to provide pharmacologically active compounds useful in the treatment of blood clotting and other related cardiovascular diseases. A further object of the invention is to provide pharmacologically active compounds which are stable analogs and/or derivatives of prostacyclin.

Another object of the invention is to provide stable biologically active prostacyclin analogues which contain an aromatic nucleus in replacement of the cyclic ether ring of natural prostacyclin. Still another object of the invention is to provide stable, biologically active prostacyclin analogues which contain as part of the aforementioned aromatic nucleus a pyridazine system. A further object of the invention is to provide stable, active prostacylin analogues which contain as part of the aforementioned aromatic nucleus a furan system, or a pyrrole system, or a thiophene system. These and other objects of the invention which will become obvious hereinafter have been attained by providing stable biologically active prostacyclin derivatives of formula VIII:

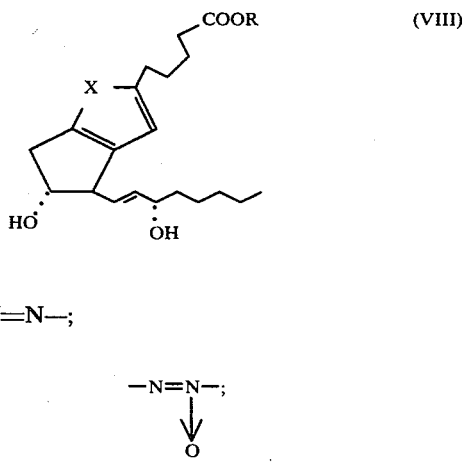

wherein
X=—N=N—;

—N=N—;
  ↓
  O and wherein R=represents hydrogen, a pharmaceutically acceptable cation or a pharmaceutically acceptable lower alkyl group.

DETAILED DESCRIPTION OF THE PREFERRED EMBODIMENTS

The compounds of the present invention comprise prostacyclin analogues of the formula

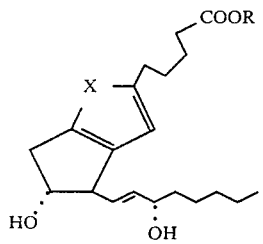

wherein X=—N=N—;

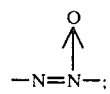

and wherein R=hydrogen or a pharmaceutically acceptable cation or a pharmaceutically acceptable lower alkyl group.

Pharmaceutically acceptable cations useful for the purposes of this invention are those with pharmaceutically acceptable metal cations, ammonium, amine cations or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, β-phenylethylamine, α-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1, 4-dimethylpiperazine, 2-methylpiperidine, and the like, as well as amines containing water-solubilizing or hydrophilic groups, e.g., mono-, di-, and tri- ethanolamine, ethyldiethanolamine, N-butylethanolamine, 2-amino-1-butanol, 2-amino-2-ethyl-1, 3-propanediol, 2-amino-2-methyl-1-propanol, tris (hydroxymethyl) aminomethane, N-phenylethanolamine, N-(p-tert-amylpenyl)diethanolamine, galactamine, N-methyl-glucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Pharmaceutically acceptable lower alkyl groups are those derived from $C_1$-$C_{10}$ hydrocarbyl residues, especially $C_1$-$C_4$. Most preferred are methyl and ethyl groups.

When X=—N=N— or —N=N(O)—, the aromaticity of the ring is given by a full sextet of π electrons.

Representative compounds within the scope of this invention are:
6,9-pyridaza prostacyclin (X=—N=N—), methyl ester and Sodium Salt
6,9-pyridaza prostacyclin —N— oxide (X=

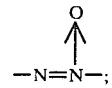

2 isomers), methyl ester and sodium salts.

The compounds of the present invention may all be prepared from a common intermediate prostanoid diketone IX. This diketone is reacted using one of the appropriate reagents a-e to obtain the cyclized products of the invention or their immediate protected precursors:

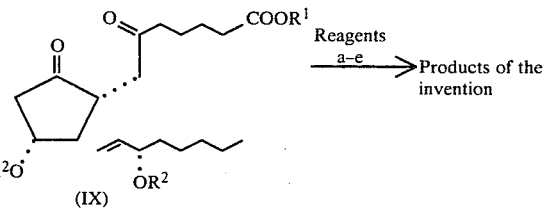

$R^1$ may be H or lower alkyl, preferably $C_1$-$C_4$ alkyl; $R^2$ may be H or a hydroxy group-protecting agent, such as an acyl group or a silyl group. Preferably $R^1$ is —$CH_3$ and $R^2$ is tert-butyldimethylsilyl or tetrahydropyran. Reagents a-e are given in Table I:

TABLE I

| Reagent | Product |
| --- | --- |
| (a) $NH_2NH_2$ followed by oxidation | Pyridaza prostacyclin |
| (b) Reagent (a) followed by further oxidation | N-oxides of pyridaza prostacyclin |

Cyclizations of diketones to yield pyridazines, furans, pyrroles and thiopenes are well known in the art. For example, the general methodology of R. M. Acheson, "An Introduction to the Chemistry of Heterocyclic Compounds", 3rd. ed., Wiley, N.Y., 1976 and references cited therein can be applied for the construction of the furan prostacyclin; for the construction of the pyrrole prostacyclin; for the preparation of thiophene prostacyclin and for the preparation of pyridazine-prostacyclin. Protecting groups on the acid functionality as well as the hydroxy functionality are preferably used to avoid side reactions which complicate the synthesis and yield mixtures of products. General methods for the protection and deprotection of hydroxy groups with acyl or silyl groups can be followed. These methods, are found for example in McOmie, Protective Groups in Organic Chemistry, (1976).

REAGENT (A)

For the preparation of the pyridaza prostacyclin, for example, diketone IX ($R^1$=lower alkyl, $R^2$=H) is treated with 0.95–1.2 equivalents, preferably 1.0 equivalents, of hydrazine at room temperature for small periods of time to obtain the corresponding 7,8-dihydro-6,9-pyridaza prostacyclin X:

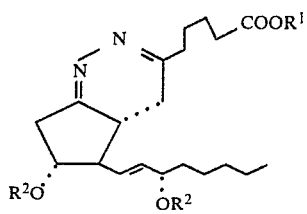

This reaction is equally successful when $R^1$ is hydrogen. It is preferable to use 95%+hydrazine for the condensation reaction. The reaction proceeds well in an organic solvent or an aqueous/organic solvent. Examples of such solvents are ethers, including cyclic ethers, alcohols, hydrocarbons, halogenated hydrocarbons, and mixtures thereof with or without water. The preferred solvents are ethers and aqueous ethers. Most preferred is tetrahydrofuran-$H_2O$ (9:1). Preferred temperatures for the reaction are $-10°$ to $+40°$ C., most preferably $+10°$ to $+30°$ C.

In order to obtain the fully aromatic pyridaza prostacyclin derivative, the 7,8-dihydro-6,9-pyridaza prostacyclin (X) ($R^1$ = lower alkyl) may be oxidized, for example over $PtO_2$, and isolated by common methods. The free acid form of 6,9-pyridaza prostacyclin VIII, (X = —N=N—, R=H) cannot be prepared from the corresponding methyl ester VIII (X = —N=N—, R = lower alkyl) by aqueous base hydrolysis in high yields, due to the base sensitivity of the compound. It is therefore prepared directly from the free acid form of the diketone prostanoid precursor IX ($R^1$=H) by similar condensation with hydrazine and oxidation. However, it is within the present invention to selectively hydrolyze the methyl ester VIII (X = —N=N—, R = lower alkyl) to the free acid or salt (R=H or cation) by a selective agent which will not destroy the remainder of the molecule.

REAGENT (B)

Further oxidation of 6,9-pyridaza prostacyclin (VIII, X = —N=N—) yields the corresponding N-oxides (VIII, X = —N=N(O)—) which are purified chromatographically as a mixture. Oxidation may be carried out with any mild oxidation agent such as m-chloroperbenzoic acid (MCPBA) or other common oxidants; (0.8–1.5 equivalents oxidant :1 equivalent of pyripyridaza compound) this reaction may be carried out with equal success on the esterified compounds or on the corresponding free acid forms. The oxidation yields about 60% yield of a 1:1 mixture of the N-oxide next to position 6, and the N-oxide next to position 9. Both the N-oxide esters (2 compounds) and the N-oxide acids (2 compounds) are stable in solution or neat under neutral conditions, although basic media leads to destruction over extended periods of time. The non-oxidized pyridaza prostacyclins are slightly more unstable. It is possible that the observed relative instability of 6,9-pyridaza prostacyclin and its oxides arises from the self-promoting tendency of the non-oxidized compound to eliminate water due to its basic nature. Removal of the basic character by oxidation to the corresponding N-oxides leads to enhanced stability.

The starting prostanoid diketones IX may be prepared by a sequence of hydrolysis and oxidation reactions on a protected prostacyclin derivative XII:

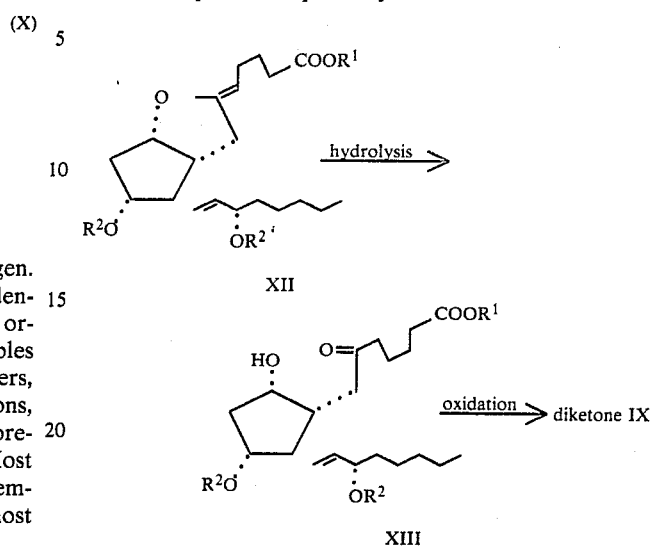

In this sequence of reactions $R^1$ is preferably a lower alkyl group and $R^2$ may be any —OH protecting group, such as trialkylsilyl, tetrahydropyranyl, acyl or the like. Preferably $R^1$ is —$CH_3$ and $R^2$ is the tetrahydropyranyl (THP) group. Prostacyclin XII may be prepared from the corresponding protected iodide XV by dehydroiodination in base.

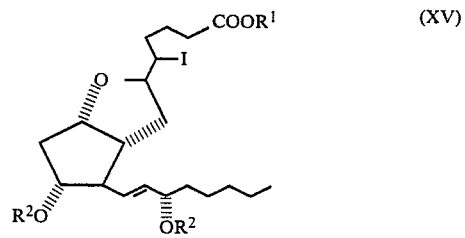

The hydroxyl-deprotected Iodide XV ($R^1$ = —$CH_3$, $R^2$ = H) has been prepared by various investigators and is readily available (Nicolaou et al., J. Chem. Soc., Chem. Comm., 630 (1977); Johnson, R, et al., J. Amer. Chem. Soc., 99, 4182 (1977); Wittaker, N., Tetr. Lett., 2805 (1977)). Standard methods of protecting hydroxy groups may be used for the protection reaction of the —OH groups of deprotected XV. The hydrolysis of prostacyclin derivative XII may be carried out in mild acid or mild base. Preferably it is performed in acid, most preferably it is carried out in acetic acid (traces)/THF (room temperature, few minutes). The oxidation of XIII to the diketone IX may be carried out with any standard oxidation reagent, such as Jones reagent or a variation thereof. Preferably the oxidant is pyridinium chlorochromate in an organic solvent, such as for example methylene chloride at room temperature; or $CrO_3$ in acetone at $-20°$ C. Yields of diketone VIII are better than 70%.

The compounds of this invention can be administered by any means that effects palliating conditions of cardiovascular complications in warm-blooded animals. For example, administration can be parenterally, subcutaneously, intravenously, intramuscularly or intraperitoneally. Alternatively or concurrently, administration can be of the oral route. The dosage administered will be dependent upon the age, health and weight of the recipient, kind of concurrent treatment if any, frequency of treatment, and the nature of the effect desired. Generally, daily dosage of active ingredient compounds will be from about 0.5 mg to 50 mg per kg of body weight. Normally, from 1 to 30 mg per kg per day, in one or more applications per day is effective to obtain the desired result. The compounds can be employed in dosage forms such as tablets, capsules, powder packets, or liquid solutions, suspensions, or elixirs, for oral administration, or sterile liquid for formulations such as solutions or suspensions for parenteral use. In such compositions, the active ingredient will ordinarily always be present in an amount of at least 0.5% by weight based on the total weight of the composition and not more than 90% by weight. Compounds of the present invention are useful in the treatment of blood clotting in heart attack cases, artherosclerosis, diabetes and cerebral strokes. They are useful in the treatment of various types of shock, such as hemorrhagic shock, in preventing gastric ulceration, by inhibiting secretion; in blood pressure regulation, and in inflammation.

Having generally described the invention, a more complete understanding can be obtained by reference to certain examples, which are included for purposes of illustration only and are not intended to be limiting unless otherwise specified.

EXPERIMENTAL METHODS OF BIOLOGICAL TESTING

Effects of prostacyclin analogs on platelet aggregation were evaluated using human and rabbit citrated platelet-rich plasma in a chronolog aggregometer at 37°. Each of the analogs was tested at two concentrations (20 mM and 2 uM) for agonistic activity (inhibition of aggregation induced by 2 uM ADP) and antagonistic activity (prevention of the inhibition of ADP-induced aggregation by 5 mM prostacyclin).

Effects of prostacyclin analogs on isolated perfused cat coronary arteries were measured as follows.

Cats of either sex (2.5–3.5 kg) were anesthetized with sodium pentobarbital (30 mg/kg) given intravenously. Hearts were rapidly excised and placed in oxygenated (95% $O_2$+5% $CO_2$) ice-cold Krebs-Henseleit (K-H) solution of the following millimolar composition: NaCl, 118; KCl, 4.75; $CaCl_2 \cdot H_2O$, 2.54; $KH_2PO_4$, 1.19; $MgSO_4.7H_2O$, 1.19; $NaHCO_3$, 12.5; glucose, 10.00. A 20-gauge stainless steel cannula was inserted into the right coronary artery via the coronary ostium. Distal to the cannula, approximately 1 cm of coronary artery was dissected free of surrounding tissue. The section of right coronary artery with the cannula in place was excised from the heart and immediately transferred to a constant flow perfusion apparatus.

The perfusion apparatus consists of a reservoir containing 20 ml of warm (37° C.) oxygenated (95% $O_2$+5% $CO_2$) K-H solution which bathes the coronary artery and serves as recirculating perfusate. An increase in perfusion pressure indicates vasoconstriction, whereas a decrease in perfusion pressure signifies vasodilation. Following an initial 1 hr. equilibrium period, vascular responsiveness was established by adding 25 mM KCl. After washing with fresh K-H solution for 20–30 mins., the preparation achieved a relatively constant low basal tone. Basal perfusion pressure averaged 50±2.5 mm Hg. Fresh K-H dilutions of stock prostacyclin analog concentrations were added to the perfusate reservoir in 0.1–0.2 ml volumes. Changes in perfusion pressure in response to prostacyclin analogue addition generally plateaus within 5 min. of administration.

EXAMPLE 1

Preparation of 6-keto $PGE_1$, methyl ester (IX, $R^1 = -CH_3$, $R^2 = H$)

1.1 Preparation of protected 11, 15 bis (THP) prostacyclin, methyl ester

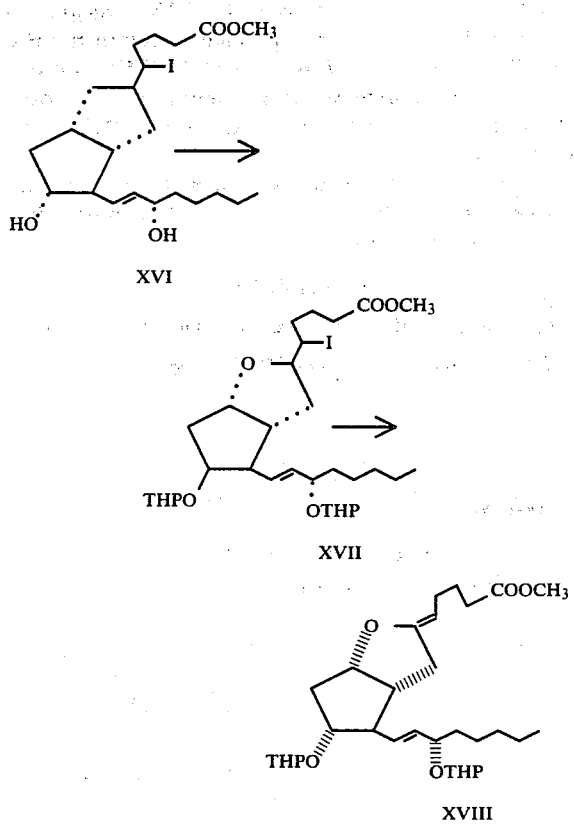

Iodide XVI was prepared as described by Nicolaou et al, in J. Chem. Soc., Chem. Comm., 630 (1977). The iodide was treated with dihydropyran (3 equivalents) in $CH_2Cl_2$ at 25° C. in the presence of 0.02 equivalents of p-toluene-sulfonic acid. The protected iodide XVII was then treated with excess DBU in toluene solution at 115° C. for 60 minutes and prostacyclin XVIII was obtained in 100% yield, by TLC.

1.2 Preparation of 6-keto PGE, methyl ester

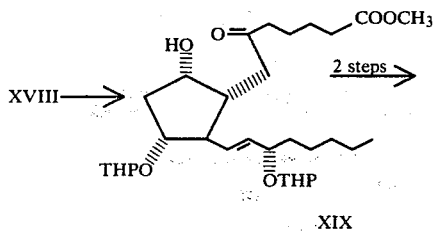

-continued

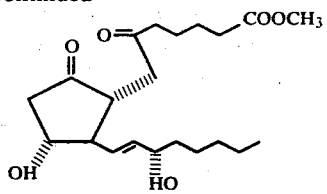

XX

Prostacyclin XVIII was treated with traces of acetic acid in wet THF at 25° C. for 15 minutes to obtain 78% of 11, 15 bis (THP)-6-keto PGF$_1$ (XIX); oxidation of XIX with 2 equivalents of pyridinium chlorochromate in CH$_2$Cl$_2$ at 25° C. led to an bis 11, 15 (THP) diketone in 76% yield which was further deprotected with AcO-H—THF—H$_2$O (3:2:2) at 45° C. to yield 90% of the diketo methyl ester XX.

This intermediate and its protected derivatives are useful for the synthesis of various of the compounds of the present invention.

EXAMPLE 2

Preparation of 6, 9-pyridaza prostacyclin, free acid 2.1 Preparation of 6-keto PGE, free acid

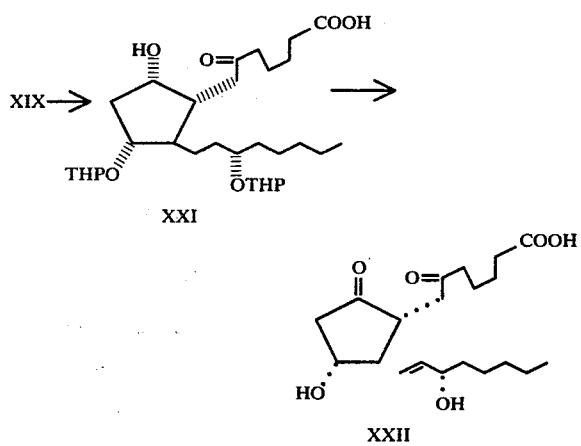

Methyl ester XIX (supra) was hydrolyzed with equivalents of LiOH in CH$_3$OH:H$_2$O (:) to yield a lithium salt which was then acidified to free acid XXI. This acid was oxidized with Jones reagent in acetone at $-20°$ C. and finally the THP groups were removed with acetic acid—THF—H$_2$O (3:2:2) at 45° C. (90% yield) to give 6-keto PGE$_1$ free acid (XXII).

2.2 Preparation of 6, 9 pyridaza prostacyclin, free acid

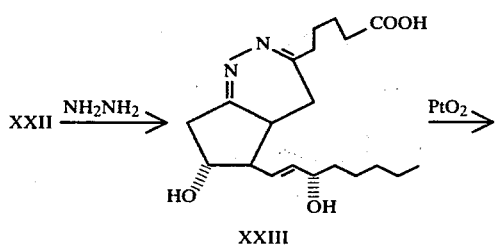

-continued

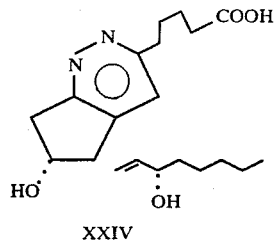

XXIV

Treatment of the diketone free acid XXII with hydrazine (1.0 equivalent, 95%+) in THF—H$_2$O (9:1) at 25° C. for 5 minutes led to a new compound XXIII (R$_f$=0.22 silica—10% CH$_3$OH in CH$_2$Cl$_2$)—This compound was directly oxidized by stirring over PtO$_2$ at 25% for 60 minutes to yield 60% of the aromatic free acid XXIV. This acid was methylated with diazomethane and isolated by careful preparative layer chromatography to avoid decomposition (R$_f$=0.24 silica—10% CH$_3$OH in CH$_2$Cl$_2$).

$^1$HNMR:

Free acid XXIV was stable in aqueous solutions at 25° C. for at least 30 days. Its biological activity as well as that of intermediate XXIII were tested by the assay described under "Experimental Methods . . . ."

The results are as follows:

| Compound | t$_\frac{1}{2}$ Saline (25°) | Biological Activity | |
|---|---|---|---|
| | | Platelet Aggregation | Cat Coronary Artery |
| Natural prostacyclin | 2 min. | Inhibitor (Potent) (1) | Dilator (Potent) (1) |
| Compound XXIV | >24h | Inhibitor (Potent) (0.5) | Dilator (Potent) (0.5) |
| Compound XXIII | >24h | Inhibitor (Potent) (0.1) | Dilator (Potent) (0.1) |

EXAMPLE 3

Preparation of 6, 9-pyridaza prostacyclin, N-oxides

Oxidation of pyridaza prostacyclin XXIV with 1.2 equivalents of m-CPBA in CH$_2$Cl$_2$ at 25° C. led to 60% of a mixture of 2 oxides XXV, $\alpha$ and $\beta$. These oxides were not separated but were purified chromatographically, R$_f$=0.34, silica—20% CH$_3$OH in CH$_2$Cl$_2$, ca 1:1 by $^1$H NMR.

The mixture of N-oxides was tested for biological activity and the results were as follows:

| | t$_\frac{1}{2}$ saline (25° C.) | Bilogical Activity | |
|---|---|---|---|
| | | Platelet Aggregation | Cat Coronary Artery |
| N-oxides XXV | >24h | Small effect | Small effect |

Having now fully described this invention, it will be apparent to one of ordinary skill in the art that many modifications and variations can be made thereto without changing the scope thereof.

What is claimed as new and intended to be covered by Letters Patent is:

1. Stable biologically active aromatic prostacyclin analogues having the formula

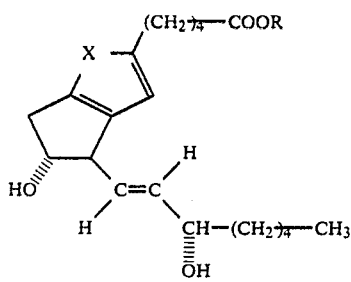

wherein X represents —N=N—, or

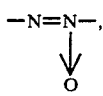

and

R represents hydrogen, a pharmaceutically acceptable cation or a pharmaceutically acceptable lower alkyl group.

2. The prostacyclin analogue of claim 1 wherein X=—N=N— and R=—CH₃.

3. The prostacyclin analogue of claim 1 wherein X=—N=N— and R=Na.

4. The prostacyclin analogue of claim 1 wherein

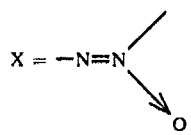

and R=—CH₃.

5. The prostacyclin analogue of claim 1 wherein

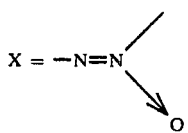

and R=Na.

6. A prostacyclin analogue of the formula

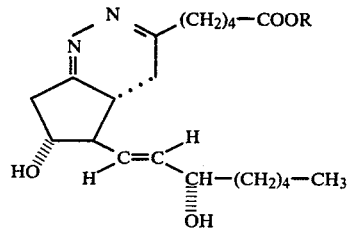

wherein R represents H, a pharmaceutically acceptable cation or a pharmaceutically acceptable lower alkyl group.

7. The prostacyclin analogue of claim 6 wherein R=—CH₃.

8. The prostacyclin analogue of claim 6 wherein R=Na.

* * * * *

UNITED STATES PATENT AND TRADEMARK OFFICE
CERTIFICATE OF CORRECTION

PATENT NO. : 4,256,883  
DATED : March 17, 1981  
INVENTOR(S) : K.C. Nicolaou et al Page 1 of 6

It is certified that error appears in the above—identified patent and that said Letters Patent is hereby corrected as shown below:

Column 3, correct the first left hand structural formula by adding the bond as follows:

Incorrect as shown in Patent

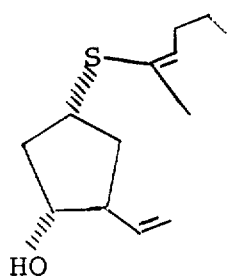

Correct formula

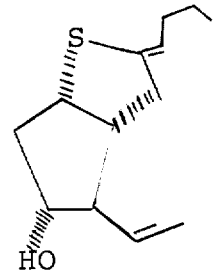

UNITED STATES PATENT AND TRADEMARK OFFICE
CERTIFICATE OF CORRECTION

PATENT NO. : 4,256,883

DATED : March 17, 1981

INVENTOR(S) : K.C. Nicolaou et al

It is certified that error appears in the above—identified patent and that said Letters Patent is hereby corrected as shown below:

Column 3, in the formulae between lines 30 and 45, please correct to include bonds as follows:

-- 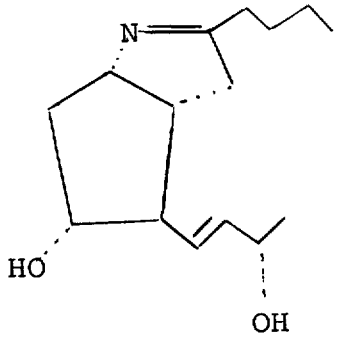 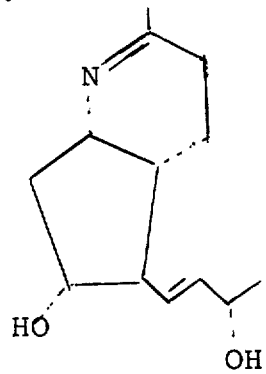 --.

(IV)  (V)

UNITED STATES PATENT AND TRADEMARK OFFICE
CERTIFICATE OF CORRECTION

PATENT NO. : 4,256,883
DATED : March 17, 1981
INVENTOR(S) : K.C. Nicolaou et al

It is certified that error appears in the above—identified patent and that said Letters Patent is hereby corrected as shown below:

Column 6, line 20, delete "a-e" and replace therefor -- a-b --.

Column 6, in the formula between lines 20 and 35, delete "a-e" and replace therefor -- a-b --; and in the same formula, insert a bond as shown below:

-- 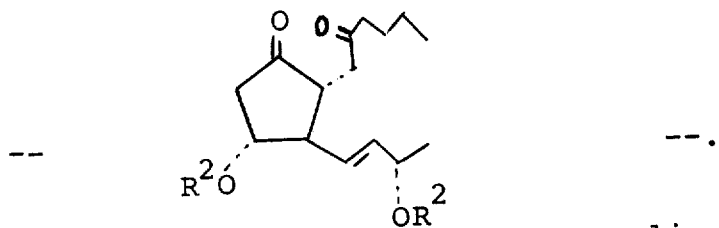 --.

Column 6, in the formula between lines 20 and 35, delete "a-e" and replace therefor -- a-b --;

Column 6, line 51, delete "the", the first and last occurrences.

Column 6, line 36, delete "a-e" and insert -- a-b --.

UNITED STATES PATENT AND TRADEMARK OFFICE
CERTIFICATE OF CORRECTION

PATENT NO. : 4,256,883

DATED : March 17, 1981

INVENTOR(S) : K.C. Nicolaou et al

It is certified that error appears in the above—identified patent and that said Letters Patent is hereby corrected as shown below:

Column 7, line 51, please delete "pyripyridaza" and replace therefor --pyridaza--;

Claim 8, in the formulae, Figures XII and XIII, add the bond to the lower portions of Figures as shown below:

-- 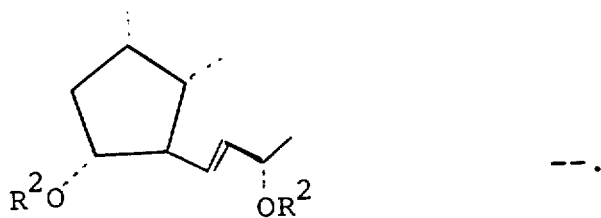 --.

Column 11, in the formula in Figure XXII, add the bond at the lower portion of the formula as shown below:

UNITED STATES PATENT AND TRADEMARK OFFICE
CERTIFICATE OF CORRECTION

PATENT NO. : 4,256,883  Page 5 of 6
DATED : March 17, 1981
INVENTOR(S) : K.C. Nicolaou et al It is certified that error appears in the above—identified patent and that said Letters Patent is hereby corrected as shown below:

-- 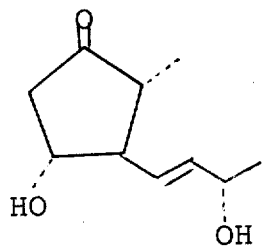 --.

Column 12, in the first formula, add the bond as shown below:

-- 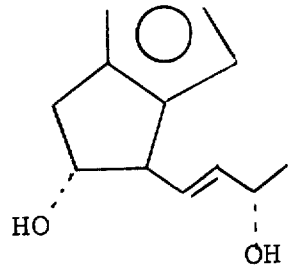 --.

UNITED STATES PATENT AND TRADEMARK OFFICE
CERTIFICATE OF CORRECTION

PATENT NO. : 4,256,883

DATED : March 17, 1981

INVENTOR(S) : K.C. Nicolaou et al

It is certified that error appears in the above—identified patent and that said Letters Patent is hereby corrected as shown below:

Column 12, line 23, please delete "$^1$HNMR:".

Signed and Sealed this

Fourth Day of August 1981

[SEAL]

Attest:

Attesting Officer

GERALD J. MOSSINGHOFF

Commissioner of Patents and Trademarks